United States Patent [19]

Behl et al.

[11] Patent Number: 4,525,339

[45] Date of Patent: Jun. 25, 1985

[54] ENTERIC COATED ORAL DOSAGE FORM

[75] Inventors: Charanjit Behl, Bloomfield; George Beskid, Upper Montclair; Navnit Shah, Clifton; Jacques Tossounian, Pine Brook; Joel Unowsky, Livingston, all of N.J.

[73] Assignee: Hoffmann-La Roche Inc., Nutley, N.J.

[21] Appl. No.: 434,452

[22] Filed: Oct. 15, 1982

[51] Int. Cl.$^3$ .................. A61K 9/62; A61K 9/36; A61K 31/43

[52] U.S. Cl. ........................ 424/16; 424/19; 424/21; 424/35; 424/38; 514/192; 514/200; 514/210

[58] Field of Search .................. 424/19–38, 424/16, 271, 246

[56] References Cited

U.S. PATENT DOCUMENTS

| | | | |
|---|---|---|---|
| 2,443,778 | 6/1948 | Romansky | 424/271 |
| 2,476,351 | 7/1949 | Binkley | 424/271 |
| 2,487,336 | 11/1949 | Hinds | 424/271 |
| 2,507,193 | 5/1950 | Buckwalter | 424/271 |
| 2,566,200 | 8/1951 | Hickey | 424/271 |
| 2,805,977 | 9/1957 | Robinson et al. | 424/38 |
| 2,864,744 | 12/1958 | Mendelsohn | 424/271 |
| 2,902,407 | 9/1959 | Gross et al. | 424/38 |
| 2,951,014 | 8/1960 | Garman | 424/271 |
| 3,016,330 | 1/1962 | Jacobsen | 424/38 |
| 3,344,029 | 9/1967 | Berger | 424/271 |
| 3,402,240 | 9/1968 | Cain et al. | 424/38 |
| 3,538,215 | 11/1970 | Snyder et al. | 424/38 |
| 3,549,746 | 12/1970 | Granatek et al. | 424/38 |
| 3,626,056 | 12/1971 | Granatek et al. | 424/271 |
| 3,639,560 | 2/1972 | Moran et al. | 424/271 |
| 3,639,605 | 2/1972 | Rule et al. | 424/271 |
| 3,655,864 | 4/1972 | Grass et al. | 424/38 |
| 3,696,189 | 10/1972 | Snyder | 424/38 |
| 3,849,569 | 11/1974 | Mead | 424/271 |
| 3,960,757 | 6/1976 | Moroshita et al. | 424/271 |
| 4,102,806 | 7/1978 | Kondo et al. | 424/38 |
| 4,145,429 | 3/1979 | Clarke | 424/271 |
| 4,250,166 | 2/1981 | Maekawa et al. | 424/81 |
| 4,338,306 | 7/1982 | Kitao et al. | 424/271 |
| 4,393,049 | 7/1983 | Horrobin | 424/271 |
| 4,401,674 | 8/1983 | Dowrick | 424/271 |

FOREIGN PATENT DOCUMENTS

| | | |
|---|---|---|
| 2654844 | 6/1978 | Fed. Rep. of Germany . |
| 52-83924 | 7/1977 | Japan . |
| 52-105220 | 9/1977 | Japan . |
| 56-104812 | 8/1981 | Japan . |
| 57-99519 | 6/1982 | Japan . |

OTHER PUBLICATIONS

Eckert et al, C.A. 89, #117875t (1978) of Ger. Offen. 2,654,844, 8 Jun. 1978.

Maeda et al, C.A. 87, #206516c (1977) of Japan Kokai, 77,83924, 13 Jul. 1977.

Yoshijima et al, C.A. 88, #79112m (1978) of Japan Kokai, 77,105,220, 03 Sep. 1977.

Sankyo Co., Ltd., C.A. 96, #110124h (1982) of Jpn. Kokai Tokyo Koho, JP 81 104812, 20 Aug. 1981.

Toyo Jozo, C.A. 97, #150726h (1982) of JP 82 99519, 21 Jun. 1982.

*Primary Examiner*—Shep K. Rose
*Attorney, Agent, or Firm*—Jon S. Saxe; Bernard S. Leon; Frank P. Hoffman

[57] ABSTRACT

There is presented a method, in the form of a dosage formulation, for transforming substantially orally inactive β-lactam antibiotics or their pharmaceutically acceptable salts or the esters, ethers, or hydrates of said antibiotics or their salts into orally active compounds by combination of the chosen β-lactam antibiotic with an enhancer comprising an aliphatic, preferably a $C_2$ to $C_{18}$, straight- or branched-chain, saturated or unsaturated, fatty acid or an aliphatic, preferably a $C_2$ to $C_{12}$, straight- or branched-chain, saturated or unsaturated, fatty acid mono-, di- or triglyceride or mixtures thereof, partial or total esters of propylene glycol, polyethylene glycol and carbohydrates of $C_2$ to $C_{12}$ fatty acids, as well as the pharmaceutically acceptable esters and ethers of said glycerides. The antibiotic and enhancer mixture may be administered orally as a solid dosage form with the β-lactam antibiotic above or, optionally, with the enhancer protected by an enteric coating.

15 Claims, No Drawings

ENTERIC COATED ORAL DOSAGE FORM

DESCRIPTION OF THE INVENTION

The present invention relates to a method for transforming substantially orally inactive β-lactam antibiotics and their pharmaceutically acceptable salts or the esters, ethers, or hydrates of said antibiotics or their salts into orally active compounds by combination of the selected antibiotic with an enhancer selected from an aliphatic, preferably a $C_2$ to $C_{18}$, straight- or branched-chain, saturated or unsaturated, fatty acid or an aliphatic, preferably a $C_2$ to $C_{12}$, straight- or branched-chain, saturated or unsaturated, fatty acid mono-, di- or triglyceride or mixtures thereof, partial or total esters of propylene glycol, polyethylene glycol and carbohydrates of $C_2$ to $C_{12}$ fatty acids, as well as the pharmaceutically acceptable esters and ethers of said glycerides.

The most preferable enhancers consist of $C_6$-$C_{12}$ saturated fatty acids or $C_{16}$-$C_{18}$ unsaturated fatty acids and $C_8$-$C_{12}$ mono-, di- or triglycerides or mixtures thereof, and edible oils containing the above and mixtures thereof, with the most preferable enhancers consisting of $C_8$-$C_{10}$ mono- and diglyceride mixtures with a substantial amount of the enhancer being the monoglyceride.

In British Patent Specification No. 1,432,784 there is disclosed a method of oral administration by combination of an orally active drug, e.g., an antibiotic and a monoglyceride or a triglyceride of a $C_6$ to $C_{12}$ fatty acid, which produced increased oral absorption. In view of this disclosure, it was unexpected when orally active β-lactam antibiotics, when combined with an enhancer, e.g., CAPMUL 8210 (a $C_8$-$C_{10}$ fatty acid mono- and diglyceride mixture), produced no increase in activity, (i.e., gastrointestinal absorption) whereas when orally inactive β-lactam antibiotics were combined with CAPMUL 8210 or MCM90 enterally and subsequently delivered orally as enteric coated dosage form, activity as manifest by therapeutically significant blood levels of the antibiotics was observed. Subsequent testing of other β-lactam antibiotics with other mixtures of mono-, di and triglycerides, their pharmaceutically acceptable salts, esters, and ethers, and fatty acids themselves confirmed this effect, as will be hereinafter illustrated.

In Belgian Pat. No. 567,598, there are disclosed an oral (as a suspension) or parenteral method of administration by combination of an antibiotic, such as a penicillin, and a fatty acid glyceride mixture, with triglycerides preferred. Applicants have found that unexpectedly superior levels of antibiotic in the blood can be achieved by the utilization of an enteric system in combination with the antibiotic/enhancer combination. This is important, since applicants' tests indicate that therapeutically unacceptable low levels of antibiotic are achieved when administering orally the combination of β-lactam antibiotic and an enhancer as a solution/suspension, as will be hereinafter illustrated.

As utilized hereinafter the term "β-lactam antibiotics" shall mean compounds having a beta-lactam ring as a central structure, i.e., the structure

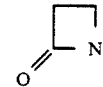

which thereafter may be substituted at various positions on the ring and/or fused with other ring systems which may themselves be substituted or unsubstituted. Some examples of well-known β-lactam antibiotics include penicillins, cephalosporins, monocyclic β-lactams, e.g. azthreonam, thienamycin and its derivatives, and the clavulanic acid derivatives as well as the pharmaceutically acceptable salts of the above-mentioned compounds.

Generally speaking, the enhancer within which the β-lactam antibiotic may be incorporated is a $C_2$ to $C_{18}$, straight- or branched-chain, saturated or unsaturated, fatty acid. Examples of such fatty acids include butyric, caproic, caprylic, capric, lauric, myristic, palmitic, stearic, lauroleic, palmitoleic, oleic, ricinoleic, linoleic, linolenic acid, etc. Also, and preferably useful are $C_2$ to $C_{12}$ straight- or branched-chain saturated or unsaturated mono-, di or triglycerides or mixtures thereof, partial or total esters of propylene glycol, polyethylene glycol and carbohydrates of $C_2$ to $C_{12}$ fatty acids, as well as the pharmaceutically acceptable esters or ethers of the glycerides.

As used herein the term "fatty acids" represents a group of saturated or unsaturated monobasic aliphatic carboxylic acids which form esters with glycerol or other alcohols to make fats, oils, waxes and other lipids.

The term "glycerides" relates to esters of glycerol, including fats and oils, in which up to three molecules of fatty acid combine with one molecule of glycerol. Although the same fatty acid is utilized in most instances, it is contemplated that glycerides of mixed fatty acids can also be used. In these instances (mixed fatty acid glycerides), it should be appreciated that optically active compounds will exist and are part of the present invention.

Also with the present invention are the esters and ethers of said glycerides. Such esters and ethers may be represented by the formulae

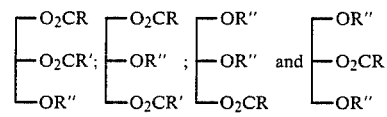

wherein R and R' represent $C_2$ to $C_{12}$ fatty acids and may be the same or different and R" represents an ester or ether group.

Suitable esterifying groups include those formed from pharmaceutically acceptable weak acids, such as tartaric acid and its diacetyl derivative, acetic, ascorbic and citric acid, or a mono-phosphate group to yield the mono-phosphate ester.

Suitable ethers may be formed by reaction of the mono- or dihydroxy function or the mono- or diglyceride with a functionally reactive lower alkyl, alkenyl, alkynyl, aryl or substituted aryl group to produce the corresponding pharamceutically acceptable ether. Such reactions are well-known in the art.

It has also been found that the polyhydric alcohols, such as a greater than $C_6$ aliphatic alcohol, e.g., octanol or a carbohydrate polyol, e.g., sucrose, are useful as enhancers in the present instance.

Two suitable test methods were utilized to test for useful enhancers, i.e., an in vivo and an in vitro test.

The in vivo test protocol consisted of the following: 250 g rats were utilized with dosing of 20 mg/kg of the β-lactam antibiotic by IV, oral and enteral routes. For oral administration the antibiotics were prepared in distilled water or in a vehicle for enhancing absorption as described above, e.g., CAPMUL 8210 or CAPMUL MCM90 (trademarks of Stokely-Van Camp Inc., Columbus, Ohio), mixtures of $C_8$-$C_{10}$ mono- and diglycerides with 70% or 90% mono-variety, respectively (α, as oleate) and given in 0.025 to 1.0 ml amounts. Intravenous administration was carried out as a control but utilizing 0.5 ml amounts. Enterally the antibiotics were prepared in distilled water or a vehicle for enhancing absorption as above. These mixtures were given in 0.025 to 1.0 ml amounts into the duodenum just below the pyloric valve. Suspensions containing 20 mg of ceftriaxone antibiotic suspended in 100 µl of CAPMUL 8210 or MCM90 encapsulated in enteric coated hard gelatin capsules were also administered orally to squirrel monkeys weighing 0.5-1 kg. Monkeys were also administered ceftriaxone in 1.0 ml amounts in water by the intravenous and enteral routes and suspended in CAPMUL 8210 or MCM90 and given enterally and orally.

Plasma levels of the antibiotics prepared in the various formulations following various routes of administration were initially measured by cardiac puncture of the rats using a heparinized syringe. Thereafter, three rats were either sacrificed and bled or only tail bled at various time periods, and the blood samples were pooled and centrifuged immediately. Squirrel monkeys were individually bled from the femoral vein or artery using a heparinized syringe. The antibiotic-containing samples were analyzed by large plate microbiological assay as set forth in articles by Lees and Tootill, *Analyst*, 80, at pages 95, 110, and 531 (1955), incorporated herein by reference. In the case of ceftriaxone, acetonitrile was used to deproteinize the sample prior to assay. The assay organism used to detect plasma levels of ceftriaxone was *E. coli* 1346.

The data in the form of blood levels of ceftriaxone in µg/ml in 250 g rats at various time periods following a 20 mg/kg body weight dose of the antibiotic in water or with enhancer is set forth in the following tables.

The first table indicates the blood levels of the ceftriaxone acid form and also the significantly greater levels on enteral administration when prepared in CAPMUL 8210 rather than in water. The second table reflects the blood levels when the sodium salt was administered intravenously in water, and again the much greater levels attained on enteral administration when prepared in CAPMUL 8210 rather than in water. Even when the sodium salt was given orally suspended in CAPMUL 8210, blood levels, though unacceptably low, were evident. This is in line with the teaching contained in the previously referenced Belgian Pat. No. 567,598. The third table shows data on the enteral absorption of the sodium salt of ceftriaxone in rats when suspended in other glyceride vehicles, including MCM90, which is reportedly quite similar to CAPMUL 8210 but contains approximately 90% monoglycerides rather than the 70% present in CAPMUL 8210.

The fourth table indicates the blood levels atained with the sodium salt of ceftriaxone in a second species, the squirrel monkey. The blood levels are shown for the salt administered intravenously in water, enterally in CAPMUL 8210 or water, orally in a suspension with CAPMUL 8210 and also in hard gelatin capsules containing 20 mg of the salt suspended in 100 µl of CAPMUL 8210 and enteric coated. As was shown in the rat, substantial blood levels were reached when the salt was given enterally in CAPMUL 8210 to the monkey and were not shown when given in water. When given orally in the CAPMUL 8210 suspension, low levels were present. When three monkeys were given enteric coated capsules containing the sodium salt and CAPMUL 8210 enhancer, good blood levels were shown in all monkeys.

TABLE 1

Levels of Ceftriaxone Acid Form - Rats

| Route Vehicle Time (min) | Enteral CAPMUL 8210* | Enteral H₂O |
|---|---|---|
| 5 | 9 | <.25 |
| 10 | 22 | 3 |
| 20 | 41 | <.25 |
| 40 | 21 | 6 |
| 60 | 12 | <.25 |
| 120 | 20 | <.25 |

*A $C_8$-$C_{10}$ mixture of mono- and diglycerides having the following characteristics:

| | Property | Limit | Test Method |
|---|---|---|---|
| Specifications | Iodine Value | 1.5 max. | AOCS Cd 1-25 |
| | Color, Lovibond Red | 2.5 max. | AOCS Cd 13b-45 |
| | Acid Value | 2.5 max. | AOCS Cd 3a-63 |
| | Moisture, KF | 0.5% max. | AOCS Ca 2e-55 |
| | Monoglycerides, α, as Oleate as Oleate | 70% min. | AOCS Cd 11-57 |
| | Free Glycerol | 2.5% max. | AOCS Ca 14-56 |
| | Residue on Ignition | 0.5% max. | USP |
| | Heavy Metals, as Lead | 10 ppm max. | USP |
| Typical Properties | Specific Gravity (100°) | 0.98–1.01 | USP |
| | Appearance | Clear Liquid | Visual |
| | Viscosity | 40–55cs | |

Capital City Products Co.
P.O. Box 569
Columbus, OH 43216

TABLE 2

Levels of Ceftriaxone Sodium Salt - Rats

| Route Vehicle Time (min) | IV H₂O | Enteral CAPMUL 8210 | | | Enteral H₂O | Oral CAPMUL 8210 |
|---|---|---|---|---|---|---|
| 5 | — | 12[1] | 12[2] | 39[3] | — | 6 |
| 10 | 132 | 26 | 23 | 44 | — | 5 |
| 20 | 112 | 40 | 31 | 21 | <.25 | <.25 |
| 40 | 79 | 12 | 25 | 8 | — | <.25 |
| 60 | 72 | 52 | 26 | 7 | <.25 | 6 |
| 120 | 25 | 18 | 18 | 6 | <.25 | 4 |
| 180 | 12 | — | — | — | — | — |
| 240 | 3.0 | — | 12 | — | 0 | — |
| 360 | <.25 | — | 8 | — | 0 | — |
| 480 | 0 | — | — | — | — | — |

[1] Three rats sacrificed and bled at each time period (plasma samples pooled).
[2] Three rats, each tail bled at every time period (plasma samples pooled).
[3] 25 µl of CAPMUL 8210 vehicle contained 5 mg ceftriaxone.

TABLE 3

Levels of Ceftriaxone Sodium Salt in Various Vehicles - Rats

| Route Vehicle Time (min) | Enteral MCM90[1] | Enteral Diacetin[2] | Enteral Monoacetin[3] | Enteral Triacetin[4] | Enteral Glyceryl[5] Monolaurate | Enteral CAPTEX[6] 300 |
|---|---|---|---|---|---|---|
| 5 | 31 | 12 | 17 | <.25 | 23 | 0 |
| 10 | 37 | 70 | 6 | 15 | 23 | 24 |
| 20 | 38 | 32 | 46 | 16 | 13 | 10 |
| 40 | 49 | 56 | 15 | 15 | 11 | <.25 |
| 60 | 42 | 15 | 21 | 23 | 17 | 3 |
| 120 | 23 | 24 | 13 | 4 | 5 | 7 |
| 180 | — | — | — | — | — | — |
| 240 | 12 | — | — | — | — | — |
| 360 | 3.8 | — | — | — | — | — |
| 480 | <.25 | — | — | — | — | — |

[1]CAPMUL MCM90 - a 90% monoglyceride variety in the $C_8$–$C_{10}$ range, similar to CAPMUL 8210 which contains 70% monoglycerides in $C_8$–$C_{10}$ range. Color Lovibond Max. = 4.0
[2]Diacetin - diglyceride of acetic acid.
[3]Monoacetin - monoglyceride of acetic acid.
[4]Triacetin - triglyceride of acetic acid.
[5]Glyceryl monolaurate ($C_{12}$).
[6]CAPTEX 300 - Medium chain triglycerides ($C_8$–$C_{10}$). - Trademark of Stokley-Van Camp, Inc. Columbus, OH
Iodine Valve = 0.5
Color Lovibond Max. = 1.0R
Acid Valve = 0.1
Cloud Point Max. = −5° C.
Moisture Max. = 0.1%
Specific Gravity = 0.927
Viscosity = 23 @ 25° C. CPS

TABLE 4

Levels of Ceftriaxone Sodium Salt - Monkeys

| Route Vehicle Time (min) | IV $H_2O$ | Enteral CAPMUL 8210 | Enteral $H_2O$ | Oral CAPMUL 8210 | Oral Enteric coated capsule[1] |
|---|---|---|---|---|---|
| 5 | 130 | 16 | — | — | — |
| 10 | 83 | 45 | — | — | — |
| 20 | 44 | 44 | 0 | 3.8 | — |
| 40 | 26 | 42 | — | — | — |
| 60 | 21 | 44 | 0 | 4.1 | 16 |
| 120 | 8 | 35 | 0 | 5.4 | 11 |
| 180 | — | — | — | 2.9 | 3 |
| 240 | — | — | 0 | 2.0 | <.25 |
| 360 | — | — | 0 | 0 | 0 |

[1]Hard gelatin capsule containing 20 mg of ceftriaxone in 100 μl of CAPMUL 8210 and enteric coated - average of three monkeys.

The same in vivo rat model and in vitro microbiological assay were employed to test for enteral enhancement of other β-lactam antibiotics in the glyceride enhancer, CAPMUL 8210. The antibiotics and the assay organisms are set forth below:

| | |
|---|---|
| cefotaxime - *E. coli* 1346 | cefoxitin - *E. coli* 1346 |
| cephalexin - *M. lutea* ATCC 9341 | moxalactam - *E. coli* ATCC 10536 |
| cefazolin - *B. subtillis* ATCC 6633 | cephalothin - *B. subtillis* ATCC 6633 |
| cefamandole - *M. lutea* ATCC 9341 | amoxicillin - *M. lutea* ATCC 9341 |
| cephradine - *M. lutea* ATCC 9341 | mezlocillin - *M. lutea* ATCC 9341 |
| penicillin G - *M. lutea* ATCC 9341 | cefoperazone - *K. pneumoniae* A |
| piperacillin - *M. lutea* ATCC 9341 | azthreonam - *E. coli* Leo HA2M4 |
| thienamycin - *S. aureus* ATCC 25923 | amdinocillin - *E. coli* Leo HA2 |

The data in the form of blood levels of each of the antibiotics in μg/ml in 250 g rats at various periods of time following a 20 mg/kg dose of the antibiotic alone in saline or water or with enhancer CAPMUL 8210 is set forth in the following tables:

TABLE 5

Levels of Cefoxitin

| Route Vehicle Time (min). | IV Saline (μg/ml) | Enteral CAPMUL 8210 (μg/ml) | Enteral $H_2O$ (μg/ml) |
|---|---|---|---|
| 5 | 59.2 | 8.8 | .7 |
| 10 | 42.6 | 7.7 | .7 |
| 20 | 24.8 | 10.5 | .8 |
| 40 | 19.0 | 10.8 | .8 |
| 60 | 9.7 | 18.2 | 1.0 |
| 120 | .2 | 9.4 | .8 |
| 240 | .2 | .7 | .6 |
| 360 | .2 | .2 | .2 |

TABLE 6

Level of Thienamycin

| Route Vehicle Time (min) | IV Saline (μg/ml) | Enteral CAPMUL 8210 (μg/ml) | Enteral $H_2O$ (μg/ml) |
|---|---|---|---|
| 5 | 45.9 | 4.1 | 0.2 |
| 10 | 20.2 | 5.4 | 0.3 |
| 20 | 11.7 | 4.3 | N.D. |
| 40 | 5.2 | 2.7 | N.D. |
| 60 | 2.1 | 3.0 | N.D. |
| 120 | .2 | .7 | N.D. |
| 240 | N.D. | N.D. | N.D. |
| 360 | N.D. | N.D. | N.D. |

TABLE 7

Levels of Azthreonam

| Route Vehicle Time (min) | IV Saline (μg/ml) | Enteral CAPMUL 8210 (μg/ml) | Enteral $H_2O$ (μg/ml) |
|---|---|---|---|
| 5 | 112 | 3.6 | 0.9 |
| 10 | 94.0 | 6.1 | 0.9 |
| 20 | 59.3 | 5.9 | 0.9 |
| 40 | 37.1 | 6.8 | 1.1 |
| 60 | 22.2 | 6.6 | 1.1 |
| 120 | 6.2 | 4.1 | 1.4 |
| 240 | N.D. | 0.9 | 0.7 |
| 360 | N.D. | 0.9 | N.D. |

N.D. = not detectable

TABLE 8

Levels of Cephalexin

| Route Vehicle Time (min) | IV Saline (μg/ml) | Enteral CAPMUL 8210 (μg/ml) | Enteral $H_2O$ (μg/ml) | Oral $H_2O$ (μg/ml) |
|---|---|---|---|---|
| 5 | 40 | 2 | 1 | N.D. |
| 10 | 40 | 2 | 3 | N.D. |
| 20 | 19 | 8 | 10 | 4 |
| 40 | 11 | 9 | 5 | 6 |
| 60 | 4 | 7 | 13 | 5 |
| 120 | N.D. | 7 | 11 | 4 |

TABLE 9

Levels of Moxalactam

| Route Vehicle Time (min) | IV Saline (μg/ml) | Enteral CAPMUL 8210 (μg/ml) | Enteral $H_2O$ (μg/ml) |
|---|---|---|---|
| 5 | 121 | 9.6 | N.D. |
| 10 | 181 | 14.0 | N.D. |
| 20 | 186 | 16.5 | N.D. |
| 40 | 84.0 | 17.9 | N.D. |
| 60 | 65.7 | 19.9 | N.D. |
| 120 | 19.9 | 17.6 | N.D. |
| 240 | 2.5 | 7.3 | N.D. |

TABLE 9-continued

Levels of Moxalactam

| Route Vehicle Time (min) | IV Saline (μg/ml) | Enteral CAPMUL 8210 (μg/ml) | Enteral H₂O (μg/ml) |
|---|---|---|---|
| 360 | N.D. | 2.5 | N.D. |

N.D. = not detectable

TABLE 10

Levels of Cephradine

| Route Vehicle Time (min) | IV Saline (μg/ml) | Enteral CAPMUL 8210 (μg/ml) | Enteral H₂O (μg/ml) | Oral CAPMUL 8210 (μg/ml) | Oral H₂O (μg/ml) |
|---|---|---|---|---|---|
| 5 | 67.3 | 3.9 | N.D. | 2.4 | 1.1 |
| 10 | 45.1 | 6.5 | N.D. | 2.9 | 1.5 |
| 20 | 20.7 | 6.5 | 2.2 | 2.6 | 1.7 |
| 40 | 18.6 | 5.5 | 3.3 | 2.1 | 2.4 |
| 60 | 9.4 | 6.3 | 5.1 | 1.2 | 3.2 |
| 120 | 2.7 | 8.2 | 7.9 | 1.8 | 6.3 |
| 240 | 1.0 | 4.4 | 7.3 | 2.8 | 3.0 |
| 360 | N.D. | 2.3 | 2.8 | — | 1.7 |
| 480 | — | — | — | 1.6 | 1.0 |

— no sample
N.D. = not detectable

TABLE 11

Levels of Cephalothin

| Route Vehicle Time (min) | IV Saline (μg/ml) | Enteral CAPMUL 8210 (μg/ml) | Enteral H₂O (μg/ml) |
|---|---|---|---|
| 5 | 114 | 9.0 | N.D. |
| 10 | 105 | 11.2 | N.D. |
| 20 | 60.1 | 11.8 | N.D. |
| 40 | 36.8 | 10.3 | — |
| 60 | 10.4 | 6.0 | — |
| 120 | 1.9 | 2.4 | N.D. |
| 240 | N.D. | N.D. | N.D. |
| 360 | N.D. | N.D. | N.D. |

N.D. = not detectable
— = no sample

TABLE 12

Levels of Cefamandole

| Route Vehicle Time (min) | IV Saline (μg/ml) | Enteral CAPMUL 8210 (μg/ml) | Enteral H₂O (μg/ml) |
|---|---|---|---|
| 5 | 50.9 | 5.9 | N.D. |
| 10 | 42.5 | 9.9 | N.D. |
| 20 | 29.2 | 12.6 | N.D. |
| 40 | 18.3 | 11.4 | Trace |
| 60 | 11.6 | 10.3 | 1.9 |
| 120 | 2.9 | 4.8 | 2.1 |
| 240 | N.D. | 1.8 | N.D. |

N.D. = not detectable

TABLE 13

Levels of Cefotaxime

| Route Vehicle Time (min) | IV Saline (μg/ml) | Enteral CAPMUL 8210 (μg/ml) | Enteral H₂O (μg/ml) | Oral CAPMUL 8210 (μg/ml) |
|---|---|---|---|---|
| 5 | 104 | N.D. | N.D. | 2.3 |
| 10 | 80 | 23 | N.D. | 1.8 |
| 20 | 42 | 14 | N.D. | 1.7 |
| 40 | 25 | 13 | N.D. | 1.1 |
| 60 | 18 | 11 | N.D. | .79 |
| 120 | N.D. | 4 | N.D. | Trace |

N.D. not detectable

TABLE 14

Levels of Cefoperazone

| Route Vehicle Time (min) | IV Saline (μg/ml) | Enteral CAPMUL 8210 (μg/ml) | Enteral H₂O (μg/ml) |
|---|---|---|---|
| 5 | 98.8 | 5.6 | N.D. |
| 10 | 66.9 | 6.1 | N.D. |
| 20 | 34.2 | 6.0 | N.D. |
| 40 | 16.0 | 7.9 | N.D. |
| 60 | 9.8 | 5.0 | N.D. |
| 120 | 1.4 | 2.5 | N.D. |
| 240 | N.D. | .8 | N.D. |
| 360 | N.D. | N.D. | N.D. |

TABLE 15

Levels of Mezlocillin

| Route Vehicle Time (min) | IV Saline (μg/ml) | Enteral CAPMUL 8210 (μg/ml) | Enteral H₂O (μg/ml) |
|---|---|---|---|
| 5 | 47.3 | 3.9 | N.D. |
| 10 | 27.4 | 5.8 | N.D. |
| 20 | 18.2 | 6.2 | N.D. |
| 40 | 8.6 | 5.0 | N.D. |
| 60 | 6.0 | 3.4 | N.D. |
| 120 | .8 | 1.2 | N.D. |
| 240 | N.D. | N.D. | N.D. |
| 360 | N.D. | N.D. | N.D. |

N.D. = not detectable

TABLE 16

Levels of Amoxicillin

| Route Vehicle Time (min) | IV Saline (μg/ml) | Enteral CAPMUL 8210 (μg/ml) | Enteral H₂O (μg/ml) | Oral H₂O (μg/ml) |
|---|---|---|---|---|
| 5 | 40.4 | 1.8 | 0.4 | 0.4 |
| 10 | 26.4 | 3.0 | 0.5 | 3.4 |
| 20 | 16.8 | 3.2 | 1.0 | 0.8 |
| 40 | 11.3 | 3.2 | 1.4 | 1.7 |
| 60 | 5.9 | 2.9 | 1.8 | 2.4 |
| 120 | 2.8 | — | 2.6 | 2.1 |
| 240 | 0.5 | 1.5 | 2.0 | 2.7 |
| 360 | 0.2 | 0.9 | 1.4 | 0.8 |

TABLE 17

Levels of Piperacillin

| Route Vehicle Time (min) | IV Saline (μg/ml) | Enteral CAPMUL 8210 (μg/ml) | Enteral H₂O (μg/ml) |
|---|---|---|---|
| 5 | 49.9 | 1.3 | N.D. |
| 10 | 28.7 | 1.4 | N.D. |
| 20 | 11.9 | 1.7 | N.D. |
| 40 | 8.5 | 1.4 | N.D. |
| 60 | 2.9 | 0.8 | N.D. |
| 120 | 1.3 | N.D. | N.D. |
| 240 | N.D. | N.D. | N.D. |
| 360 | 2.8 | N.D. | N.D. |

N.D. = not detectable

TABLE 18

Levels of Cefazolin

| Route Vehicle Time (min) | IV Saline (μg/ml) | Enteral CAPMUL 8210 (μg/ml) | Enteral H₂O (μg/ml) |
|---|---|---|---|
| 5 | 105 | 8 | N.D. |
| 10 | 91 | 13 | N.D. |
| 20 | 81 | 21 | N.D. |
| 40 | 50 | 14 | N.D. |
| 60 | 32 | 11 | N.D. |
| 120 | N.D. | N.D. | N.D. |

TABLE 19

| | Levels of Amdinocillin | | |
|---|---|---|---|
| Route | IV | Enteral | Enteral |
| Vehicle | Saline | CAPMUL 8210 | $H_2O$ |
| Time (min) | (μg/ml) | (μg/ml) | (μg/ml) |
| 5 | 65.5 | 3.0 | N.D. |
| 10 | 47.7 | 3.5 | 0.3 |
| 20 | 24.3 | 4.2 | 0.3 |
| 40 | 10.0 | 5.3 | 0.3 |
| 60 | 5.4 | 6.0 | 0.3 |
| 120 | 1.0 | 4.1 | N.D. |
| 240 | N.D. | 0.8 | N.D. |
| 360 | N.D. | 0.3 | N.D. |

N.D. = not detectable

TABLE 20

| | Levels of Penicillin G | | | | | |
|---|---|---|---|---|---|---|
| Route | IV | Enteral | Enteral | Subcutaneous | Oral | Oral |
| Vehicle | Saline | CAPMUL 8210 | $H_2O$ | $H_2O$ | CAPMUL 8210 | $H_2O$ |
| Time (min.) | (μg/ml) | (μg/ml) | (μg/ml) | (μg/ml) | (μg/ml) | (μg/ml) |
| 5 | 74.2 | 7.0 | 0.6 | 4.9 | — | — |
| 10 | 45.5 | 7.8 | 0.5 | 11.1 | 4.1 | 2.5 |
| 20 | 18.6 | 9.5 | 0.7 | 15.9 | 7.4 | 2.2 |
| 40 | 9.9 | 10.4 | 0.9 | 9.6 | 3.4 | 3.4 |
| 60 | 3.2 | 10.5 | 1.5 | 4.1 | 2.5 | 2.3 |
| 120 | 0.4 | 6.2 | 1.6 | 0.5 | *0.5 | 1.0 |
| 240 | N.D. | 2.5 | 1.1 | N.D. | N.D. | *0.7 |
| 360 | N.D. | 0.4 | 0.8 | N.D. | N.D. | N.D. |

N.D. = not detectable
— = no sample

As discussed previously, the use of enhancer did not increase the plasma levels of cephalexin and cephradine, which were the two orally active cephalosporins tested, nor amoxicillin, an orally active penicillin. Enhancement, i.e., intestinal (enteral) absorption, was imparted to the other previously orally inactive β-lactam antibiotics tested, using CAPMUL 8210 or MCM90. As was demonstrated for ceftriaxone, the β-lactam antibiotics showed enhanced enteral absorption with CAPMUL 8210 or similar vehicles. They could be similarly administered orally as solid dosage forms with the β-lactam antibiotic and the enhancer protected by an enteric coating.

As an active dosage, a range of about 25 to about 2000 mg, preferably about 50 mg to about 500 mg of β-lactam antibiotic in the enhancer vehicle is preferred for humans.

An in vitro model for determining transport characteristics and therefore possibly identifying useful vehicles for delivery of the β-lactam antibiotics consists of a cell measuring the permeability of synthetic membrane in various vehicles and at different drug concentrations. Two articles incorporated herewith by reference set forth the basic model utilized, i.e., Behl et al., *Journal of Investigative Dermatology*, 75, p. 346-352, 1980 and Durrheim et al., *Journal of Pharmaceutical Sciences*, 69, No. 7, p. 781-786, 1980. The synthetic membrane utilized is a siloxane fluid membrane. The cell consists of a container having two compartments with the membrane in between the compartments. In the receiving compartment there is pH 7.4 buffer (Clarks-Subs buffer), and in the donor compartment there are the selected transport vehicles, i.e., CAPMUL 8210, diacetin, etc., with a $C_1$ to $C_8$ alkanol as a lipophilic-increasing agent. Radiolabeled β-lactam antibiotic is placed in the donor compartment. Starting at zero time, samples are withdrawn from the receiving compartment at selected intervals. The drug amounts as a function of time in the receiving compartment are measured and plotted. The plot is linear and is used to compute the permeability coefficient (P value) in accordance with Fick's First Law of Diffusion. A buffer/buffer control is utilized for comparison purposes. The effectiveness of the vehicle is a function of the P value, i.e., those values obtained which are greater than that of the buffer/buffer control indicate enhancement.

The permeability coefficients of various enhancer vehicles in a 50% mixture with CAPMUL 8210 are as follows:

| Donor Medium (50% CAPMUL & 50% Enhancer) Adjuvant | $P \times 10^6$ (cm/hr.)* 1st |
|---|---|
| monoacetin | 47.20 |
| diacetin | 27.10 |
| triacetin | 15.80 |
| CAPMUL 8210 | 9.10 |
| CAPTEX 300 | 20.50 |
| control | 3.3 |

*Initial slopes

As noted previously, the method of administering the β-lactam antibiotic and enhancer is in the form of an enteric coated entity, i.e., as a solid dosage form, in order to protect the β-lactam antibiotic from the acidity of gastric fluid. The vehicles are usually in liquid form but can be in solid form. They may be filled in hard- or soft-shell capsules, or the liquid vehicle can be absorbed on carriers, e.g., starch, to make free flowing powders and then filled in the above capsules or compressed into tablets with appropriate enteric coating.

Other dosage forms may include enteric coated or nonenteric coated delivery systems, i.e., capsules or tablets, wherein the β-lactam antibiotic and enhancer may be enteric coated themselves. The enteric coating of individual β-lactam antibiotics and/or enhancer may be achieved by utilization of microencapsulated forms of the β-lactam and/or enhancer to make a free-flowing powder for filling into hard- or soft-shell capsules or which may be compressed into tablets. Also envisioned herein would be an enteric coated microcapsule or beadlet form of the β-lactam antibiotic either alone or suspended in liquid enhancer which may thereafter be encapsulated in an enteric or nonenteric coated capsule.

The above drug delivery systems are coated with enteric coating materials to protect, for the most part, the β-lactam antibiotic from the gastric fluid and also to attain optimal delivery of β-lactam and enhancer to the intestine. The enteric coating material is not affected by gastric fluid, but it dissolves in the intestinal fluid, releasing the drug. The efficacy of these enteric coated products can be determined by known USP methods.

The enteric coating materials among others are:
Cellulose acetate phthalate
Hydroxypropyl methylcellulose phthalate
Polyvinyl acetate phthalate
Shellac
Methacrylic acid and Methacrylic acid esters
Zein
Other materials known in the art These enteric coating materials may be applied with or without plasticizers, such as acetylated glycerides, diethylphthalate, etc., and by means known in the art.

EXAMPLES OF ENTERIC COATING SOLUTIONS ARE

| | % w/w |
|---|---|
| A | |
| Hydroxypropyl methylcellulose phthalate (HPMCP) | 5. |
| Triacetin | 0.5 |
| Methylene chloride | 47.25 |
| Denatured alcohol | 47.25 |
| B | |
| HPMCP | 10. |
| Titanium dioxide | 0.2 |
| Dimethyl polysiloxane | 0.05 |
| Acetone | 44.875 |
| Denatured alcohol | 44.875 |
| C | |
| Cellulose acetate phthalate (CAP) | 8.5 |
| Diethyl phthalate | 1.5 |
| Titanium dioxide | 0.2 |
| Acetone | 44.9 |
| Denatured alcohol | 44.9 |
| D | |
| Polyvinyl acetate phthalate | 5. |
| Acetylated glycerides | 0.8 |
| Methylene chloride | 47.1 |
| Denatured alcohol | 47.1 |
| E | |
| Eudragit S or L* | 8 |
| Acetone | 46 |
| Anhydrous alcohol | 46 |
| Plasticizer | qs |

*Eudragit S or L are brand names (Rohm. Pharma., GMBH, Weiterstadt, W. Germany) for methacrylic acid or methacrylic acid esters.

The percentage of coating applied is between about 1–10%, with the most desirable amount being about 2 to 8% of the capsule or tablet weight.

In any formulation useful ratios of β-lactam antibiotic to vehicle range from about 1:32 to about 1:0.5, with a preferred ratio being about 1:16 to 1:3, with most preferred being about 1:8. As noted previously, meaningful antibiotic levels in the rat model included ratios of antibiotic to vehicle of up to about 1:100.

The combination may also include adjunct materials known in the art in order to make a desirable consistency.

The enteral formulations may take the form of solid or liquid formulations for oral application. Thus, the formulations may be in the form of enteric coated capsules, coated tablets or regular capsules or tablets containing an enterically microencapsulated mixture of enhancer and β-lactam antibiotic or the two entities may be enteric coated separately. These formulations may, in addition, contain conventional pharmaceutical carriers and additives, especially viscosity-improving and/or structure- or matrix-forming additives which provide for an appropriate viscosity and physical structure. Suitable additives are, e.g., thickening agents, such as highly dispersed silicic acid (e.g., the commercial products "Aerosil") bentonites, colloidal clay, carboxymethyl celluloses, modified montmorillonites, such as alkyl ammonium salts of montmorillonites (e.g., the commercial products "Bentone") wherein the alkyl groups contain 16 to 18 carbon atoms, organic thickening and structure-forming agents, such as saturated higher fatty acids and alcohols containing, e.g., 12 to 20 carbon atoms, such as stearic or palmitic acid, stearic or cetylic alcohol, waxes like beeswax, synthetic esters of higher fatty acids and higher fatty alcohols, or spermaceti, monoglycerides of saturated or unsaturated high fatty acids, e.g., monoglycerides of stearic acid, palmitic acid or oleic acid, partial glycerides of fatty polyhydroxy acids (e.g., the commercial products "Softigen 701"), gelling agents, such as aluminum stearate, dispersing agents, such as anionic, nonionic and cationic surfactants, emulsifying agents, such as lecithin, and like salts. The compositions may further comprise pharmaceutical adjuvants, e.g., binders or lubricants for tableting, stabilizing agents, e.g., EDTA, antioxidants, e.g., ascorbic acid, flavoring agents, preservatives, e.g., methyl or propyl parabens and buffering agents, e.g., phosphates. Useful coloring agents include the acceptable FD & C dyes. Useful opacifiers include titanium dioxide.

What is claimed:

1. An orally administered enteric coated pharmaceutical composition which consists essentially of from about 50 to 500 mg of beta-lactam antibiotic distributed in at least about 33% by weight of an enhancer consisting of a $C_2$ to $C_{12}$ glyceride mixture of at least one glyceride selected from the group consisting essentially of monoglycerides, diglycerides and triglycerids of fatty acids of $C_2$ to $C_{12}$ chain length and mixtures thereof and adjuvants suitable for oral enteric administration.

2. The composition of claim 1, wherein the glyceride or mixture of glycerides is of $C_8$ to $C_{12}$ fatty acids.

3. The composition of claim 2, wherein the glyceride mixture is between about 33° to about 98% by weight of the composition.

4. The composition of claim 3, wherein the glyceride mixture is about 89% by weight of the composition.

5. A method of beta-lactam antibiotic treatment which comprises orally administering to a warm blooded animal a readily absorbable enteric coated pharmaceutical composition which consists essentially of from about 50 to 500 mg of a beta-lactam antibiotic distributed in at least about 33% by weight of an enhancer consisting of an absorption enhancing amount of a $C_2$ to $C_{12}$ glyceride mixture of at least one glyceride selected from the group consisting essentially of monoglycerides diglycerides and triglycerids of fatty acids of $C_2$ to $C_{12}$ chain length and mixtures thereof and adjuvants suitable for oral enteric administration.

6. The composition of claim 5, wherein the glyceride or mixture of glyceride is of $C_8$ to $C_{12}$ fatty acids.

7. The composition of claim 6, wherein the glyceride mixture is between about 33% to about 98% by weight of the composition.

8. The composition of claim 7, wherein the glyceride mixture is about 89% by weight of the composition.

9. The composition of claim 1 wherein the dosage form is an enteric coated capsule, microcapsule or beadlet.

10. The composition of claim 1 wherein the dosage form is a tablet.

11. An absorbable pharmaceutical composition which comprises a therapeutically effective amount of ceftriaxone distributed in a vehicle comprising an absorption enhancing amount of a $C_8$ to $C_{10}$ mixture of mono- and diglycerides wherein the monoglyceride content may be about 70% or about 90% respectivley, said composition being enterally administered.

12. The method of claim 5 wherein the dosage form is an enteric coated capsule, microcapsule or beadlet.

13. The method of claim 5 wherein the dosage form is an enteric coated tablet.

14. A method of β-lactam antibiotic treatment which comprises orally administering to a human being a readily absorbable enteric coated pharmaceutical composition which comprises a therapeutically effective amount of a β-lactam distributed in a $C_8$ to $C_{10}$ mixture of mono- or diglycerides wherein the monoglyceride is present as about 70% or about 90% of the mixture in an enteric coated entity selected from an enteric coated capsule or tablet or a capsule having enterically coated microencapsulated ceftriaxone in said glyceride mixture.

15. The composition of claim 9 wherein the vehicle is a $C_8$ to $C_{10}$ mixture of mono- or diglycerides wherein the monoglyceride is present as about 70% or about 90% of the mixture.

* * * * *